United States Patent [19]

Petersen

[11] Patent Number: 4,524,766
[45] Date of Patent: Jun. 25, 1985

[54] SURGICAL KNEE ALIGNMENT METHOD AND SYSTEM

[76] Inventor: Thomas D. Petersen, 9680 Alto Dr., La Mesa, Calif. 92041

[21] Appl. No.: 337,587

[22] Filed: Jan. 7, 1982

[51] Int. Cl.$^3$ .............................................. A61F 5/04
[52] U.S. Cl. ............................... 128/92 H; 128/92 E
[58] Field of Search ........... 128/92 E, 92 EA, 92 EB, 128/92 R, 303 R, 317, 305, 92 H

[56] References Cited

U.S. PATENT DOCUMENTS

D. 245,918  9/1977  Shen ............................. 128/92 EB
2,301,500  11/1942  Anderson ...................... 128/92 EB

OTHER PUBLICATIONS

Insall et al., Zimmer Brochure B-251-2, 1980.
Groth et al., Zimmer Brochure B-271, 1978.
Hungerford et al., Howmedica Brochure H2026, 1980.
Groth, Harry, MD et al., (Zimmer USA); "Multi-Radius Total Knee"; Feb. 1979, pp. 7-10, 17-23; 26-30; 32-35; 38 & 39.
De Puy Div. of Biodynamics; "The Townley Anatomic Knee System", p. 5, Feb. 1978.
Walker, P. S. Ph.D.; "Howmedica Surgical Techniques", 1980.
"R.M.C. Total Knee System", Richards Mfg. Co., 1978.

Primary Examiner—C. Fred Rosenbaum
Assistant Examiner—C. W. Shedd
Attorney, Agent, or Firm—Sherman & Shalloway

[57] ABSTRACT

A system of precision instruments for utilization in knee surgery, particularly for component replacement includes a series of alignment and cutting guides which function to align various necessary cuts of bone structure with respect to the ankle. The system in its preferred arrangement includes a cutting guide head mounted on an elongated, extensible support frame member having a laterally adjustable ankle guide for adjustably aligning the cutting heads for a proper angle of cut with respect to the weight bearing axis through the ankle and the hip joint. A tibial resection guide head with a cutting guide slot is fixed to the upper end of the elongated extensible support frame member and including a traction grip extending outward from the extendable support frame member for application of traction or tension to the collateral ligaments. An anterior femoral condyle resector/posterior spacer guide is applied to the anterior femoral cortex superior to the anterior condyles, and is used to accurately remove the anterior femoral condyles and predetermine the size of the optimal tibial prosthesis. A distal femoral condyle resector guide is detachably mountable on the frame and includes a cutting guide head for guiding a cut of the distal femur that is aligned with the tibial plateau. A posterior femoral condyle resector/chamfer guide is a template, the actual size of the prosthesis, that provides the surgeon with a visual guide to properly fit the prosthesis on the distal femur, and not only allows for precision cuts on the distal femur but allows the surgeon to make rotational and spacing adjustments at this final stage. A weight bearing axis alignment guide for alignment of the support frame member includes a bracket with an indicator for positioning above the hip joint and a flexible line for extending to the ankle bracket for alignment over the center of the femoral head. A system of tamps and broaches, in conjunction with a drill guide, is used to make precision cuts on the resected tibial and femoral surface, and provides the optimal amount of space around the various stems of the prosthesis, for bone cement.

50 Claims, 19 Drawing Figures

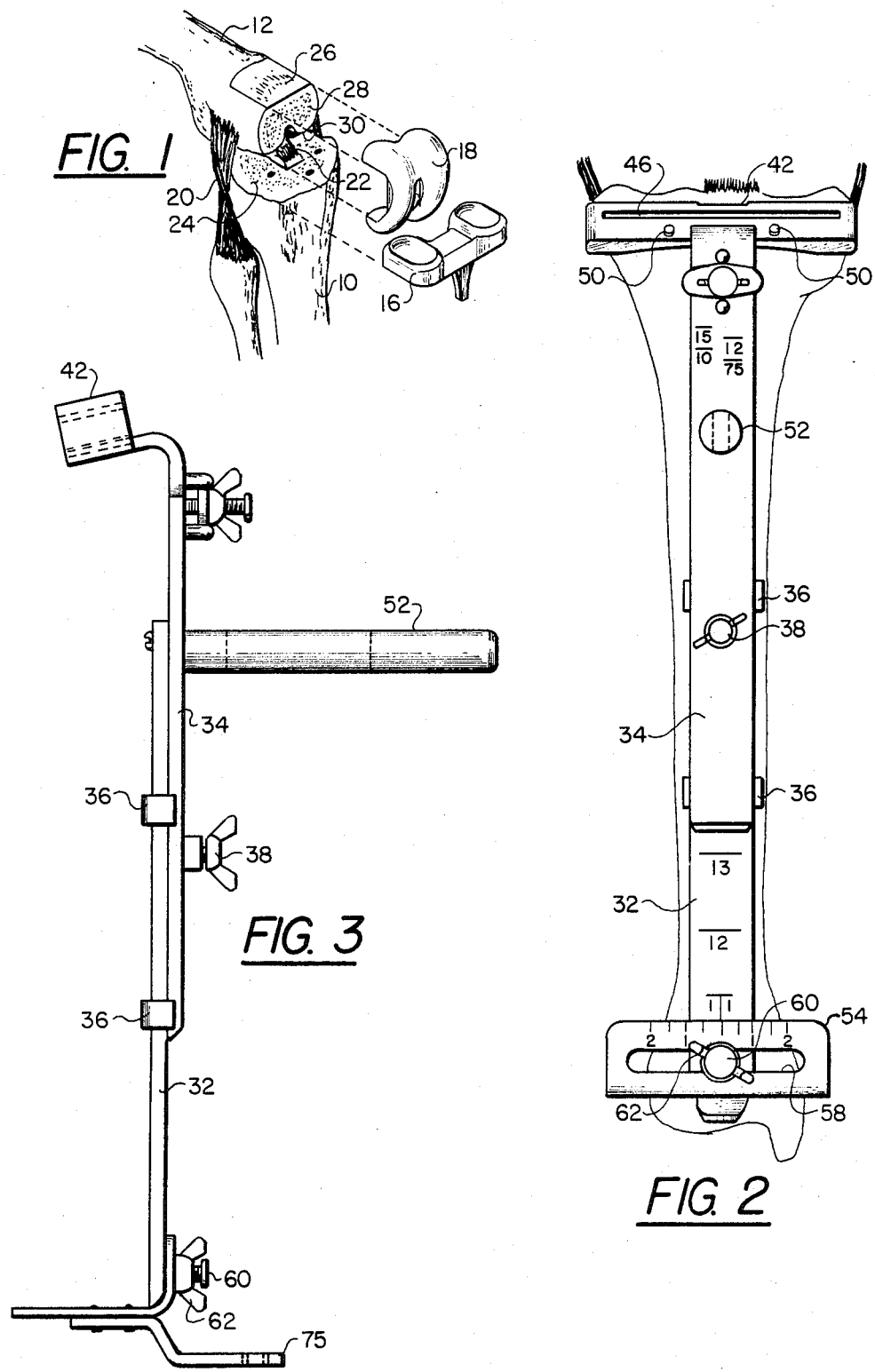

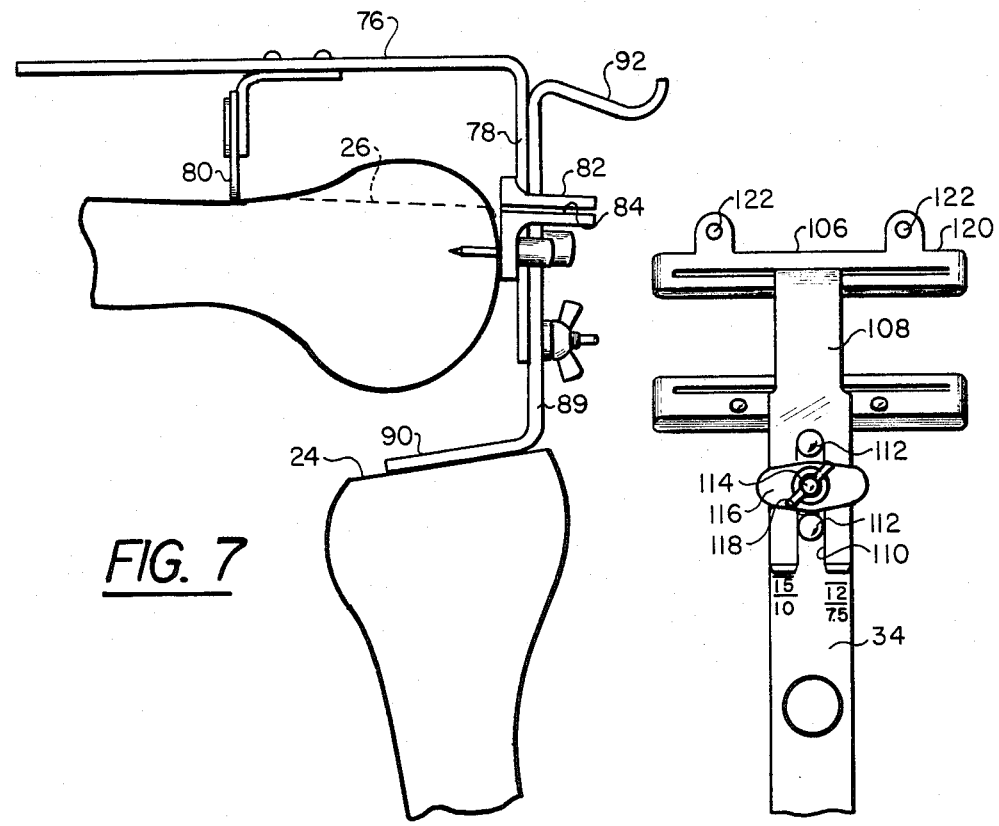
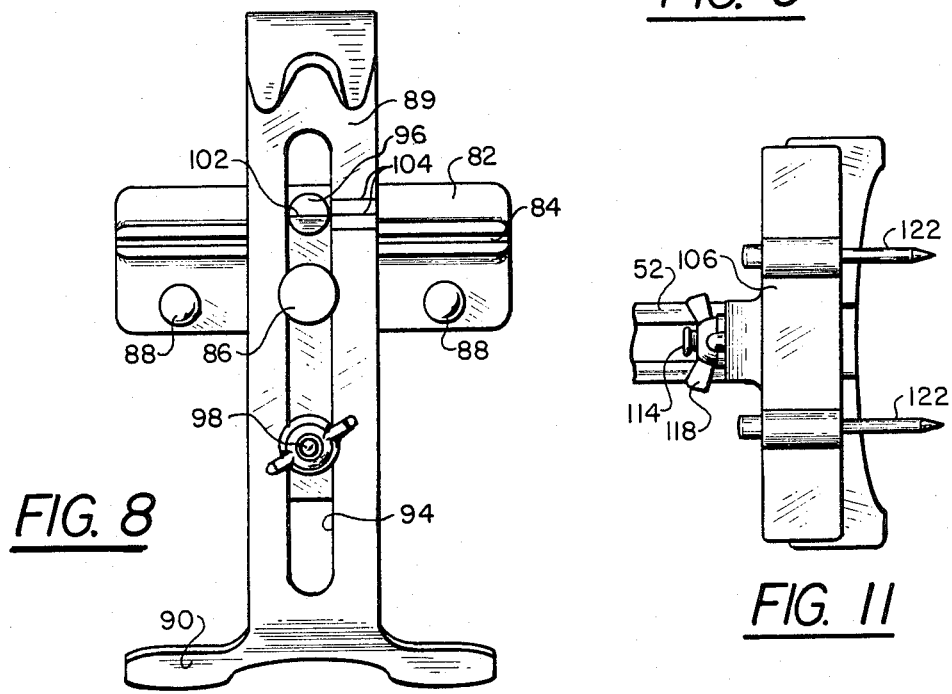

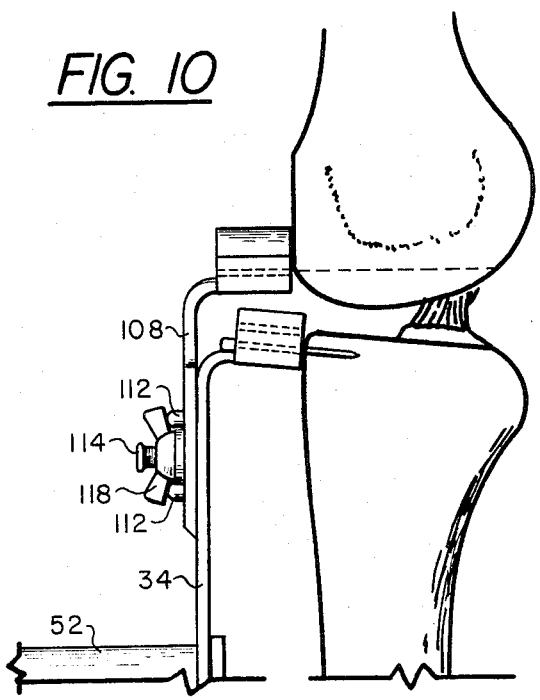
FIG. 10
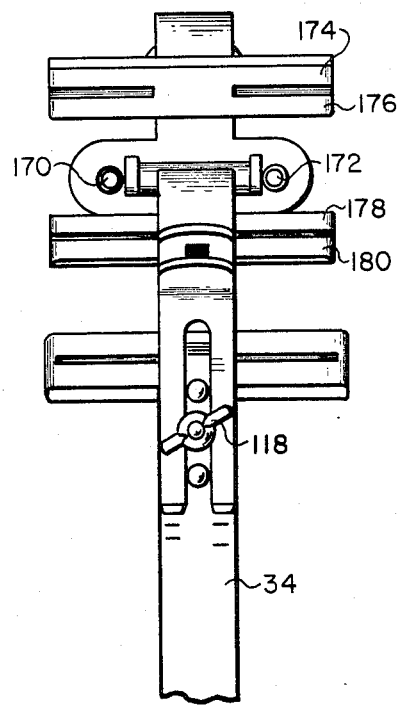
FIG. 14
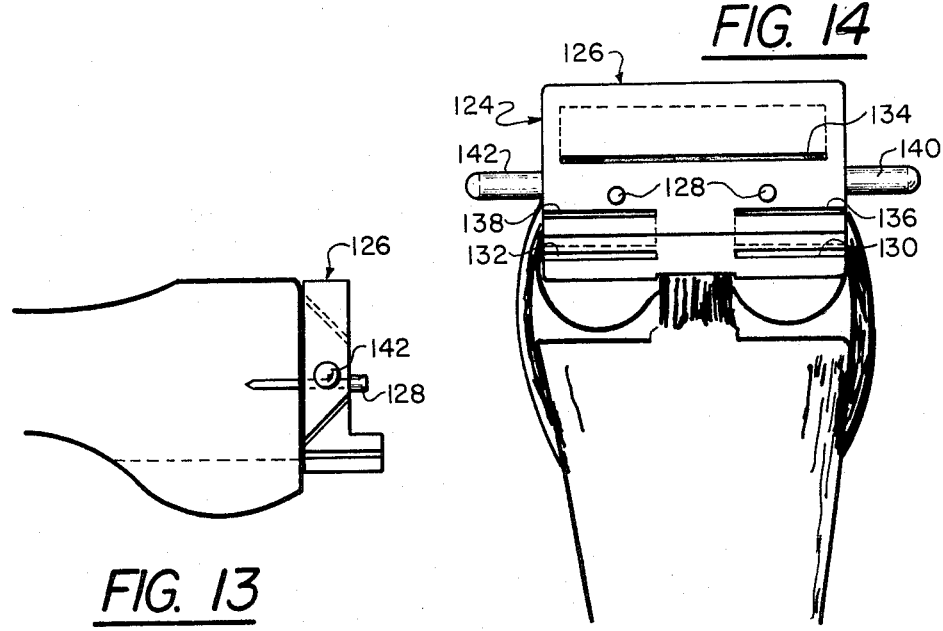
FIG. 13
FIG. 12

SURGICAL KNEE ALIGNMENT METHOD AND SYSTEM

BACKGROUND OF THE INVENTION

The present invention is directed to surgical methods and instruments and pertains particularly to an improved instrument system for providing improved accuracy for knee surgery.

Knee surgery for the repair and/or replacement of knee joints has become common practice today. The total replacement of the knee joints has become practical because of recent improvement in the construction of total knee structures which closely mimic the natural knee in movement.

A problem with such total knee replacement, however, is that current surgical instruments and techniques require an extremely high degree of skill on the part of the surgeon in order to achieve proper fitting and alignment of the knee structures. The skill necessary to achieve optimum fitting and alignment may in many cases, come only from extensive experience.

It is therefore desirable that effective system of instruments and method of knee surgery be available that insures a high degree of success in fitting and alignment.

SUMMARY AND OBJECTS OF THE INVENTION

It is the primary object of the present invention to provide an improved instrument system and method for performing knee surgery.

In accordance with the primary aspect of the present invention, a system of instruments, including a tibial resection alignment guide and a distal femoral condyle resection guide includes a common support frame with alignment means for alignment, along the weight bearing axis, with reference to the ankle, to properly align or realign, the cuts on the tibia and femur. An anterior femoral condyle resector/posterior spacer guide accurately determines the proper anterior femoral condyle resection and mathematically determines the optimal tibial prosthesis height. A posterior femoral resector/chamfer guide is properly placed to correct any rotational deformity and size differences for optimum resection of the distal femur. The method of the invention includes a preferred sequence of operation, performed with specified instruments, including tibial resection utilizing an adjustable tibial resection guide to achieve optimum alignment, an anterior femoral resector/posterior spacer guide, a distal femoral condyle resection achieved with reference to the tibial resection and the ankle guide in order to obtain optimum alignment, a posterior femoral condyle resection utilizing a combined posterior femoral condyle resector/chamfer guide with all instruments utilizing the same basic support structure as a reference.

BRIEF DESCRIPTION OF THE DRAWINGS

The above, and other objects and advantages of the present invention, will become apparent from the following description when read in conjunction with the drawings, wherein:

FIG. 1 is a perspective view of a knee joint prepared in accordance with the invention with a new prosthesis positioned for attachment.

FIG. 2 is a front elevation view showing the tibia and tibia resection guide in position.

FIG. 3 is a side elevation view of the instrument of FIG. 2.

FIG. 7 is a side elevation view of an anteriorfemoral condyl resector/posterior spacer guide shown in position for use.

FIG. 8 is a front elevation view of the anterior femoral condyle resector/posterior spacer guide of FIG. 7.

FIG. 9 is a front elevation view of a distal, femoral condyle resection guide in accordance with the invention.

FIG. 10 is a side elevation view of the embodiment of FIG. 9 shown in position for use.

FIG. 11 is a top plan view of the guide of FIG. 9.

FIG. 12 is a front elevation view of a posterior femoral condyle resector/chamfer guide.

FIG. 13 is a side elevation view of the guide of FIG. 12.

FIG. 14 is a front elevation view of a combined anterior/posterior femoral condyle resection guide.

DETAILED DESCRIPTION OF PREFERRED EMBODIMENTS

Figure 4:
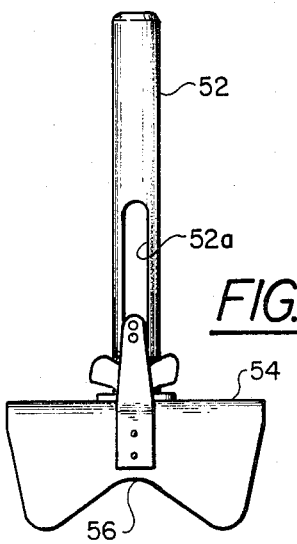
FIG. 4 is a bottom view of the instrument of FIG. 3.

Turning to the drawings, with particular reference first to FIG. 1, there is illustrated, a knee joint which has been prepared in accordance with the present invention utilizing the instruments thereof. As illustrated, the tibia 10 is illustrated as extending at approximately a 90 degree angle with the femur 12 with the tibia and femur resectioned to provide mounting surfaces for mounting a tibial implant of prosthesis 16 and a femoral implant or prosthesis 18. These implants are of the types referred to as a total knee and obtainable for example from the Zimmer Corporation in Warsaw, Ind. under the trademark "Multi-Radius". These knee instruments and the operation performed on the knee have been designed to permit a complete preservation of both the collateral ligaments 20 and the cruciate ligaments 22.

The tibia has been prepared and resectioned removing a portion of the plateau to provide an eight degree posterior slanted surface 24 for receiving the implant 16. In a similar manner the femur has been resectioned to provide series of planar surfaces 26, 28 and 30 as a result of resection of the femoral condyles for receiving femoral condylar implant 18. While only the bone and ligament structure will be illustrated herein, it will be understood that during normal operation muscles and skin of the leg structure will be in place with proper incision made to provide access to the knee structure. The FIG. 1 illustration signifies a finished cut joint structure ready to receive the implants 16 and 18. The remaining illustrations throughout this application will be that of the illustrated structures at various stages of operation preceding the condition illustrated in FIG. 1.

It should also be understood that numerous instruments and fixtures, not specifically illustrated and perhaps not mentioned, may be utilized during the operation. Many of such instruments, and their cooperative relationship to those illustrated, will be discussed throughout the specification, where necessary, in order to provide an understanding of the instruments herein and the operation. Certain normal procedures which will be utilized in the operation may be omitted from this discussion with the understanding that no attempt will be made herein to specify each and every detail of the procedure.

In preparation for the operation, the knee is prepared and draped in the usual manner, and preferably, the knee is supported during operation in a knee holder such as described in my U.S. Pat. No. 4,136,858 issued Jan. 30, 1979 entitled "Surgical Knee Holder". The use of this knee holder has many advantages, including holding the operative knee in 90 to 120 degrees of flexion and/or 15 to 20 degrees of internal or external rotating during the operation. After the knee has been prepared and appropriate incisions made to provide access to the area of the knee joint, the tibial plateau cut is made first. In carrying out this part of the operation the tibial jig or resection guide as illustrated in FIGS. 2-4 is used. As illustrated in FIG. 2, the tibial resection guide comprises an elongated central extensible body member defined by first or lower body member 32 and a second or upper body member 34, adjustably secured to the first member by means of a suitable retainer such as a clamping screw 38 thereon. The members slide upon each other such as by L-shaped brackets 36 which are secured to member 34 and extend around member 32 and permits adjustment of the length of the body member. The lower member is marked at one inch increments, with the lower edge of member 34 being an indicator which when related to a mathematical table correlates with indicia on the ankle bracket.

A guide head 42 is secured to the curved upper end of the member 34 and includes a laterally extending guide slot 46. The guide head member 42, includes a pair of retaining pins 50, extending through bores in the head member 42 for anchoring the head member in position on the tibia. The slot 46, as will be seen in FIG. 3, extend downward at an 8 degree angle from the axis of the main body 34 to give a posterior tilt. This slot guides a saw for cutting the tibia plateau at the proper angle to provide the surface 24, as illustrated in FIG. 1. An outwardly extending handle 52 permits manipulation and handling of the cutting guide member and application of traction to the ligaments.

The lateral angle of the cut may be adjusted by alignment with the ankle and adjustment relative thereto. This is achieved by means of an ankle guide assembly comprising an ankle bracket member 54 adjustably secured to the lower end of the extensible body member 32, and having a laterally adjustable horizontally extending V-slotted guide portion 56 for engagement of the ankle area of the tibia as illustrated in FIGS. 3 and 4. The laterally adjustable bracket 56 includes a horizontally extending slot 58 for receiving a stud or bolt 60 mounted on member 54 and extending through the slot with a wing nut or the like 62 mounted thereon. Indicia marks above the slot 58, in conjunction with the particular length of the body member 32, 34 indicates the specific angle of the slot 46 with respect to the ankle and/or axis of the tibia for obtaining proper weight bearing alignment. This permits adjustment of the jig for correcting valgus or varus of the knee.

Figure 5:
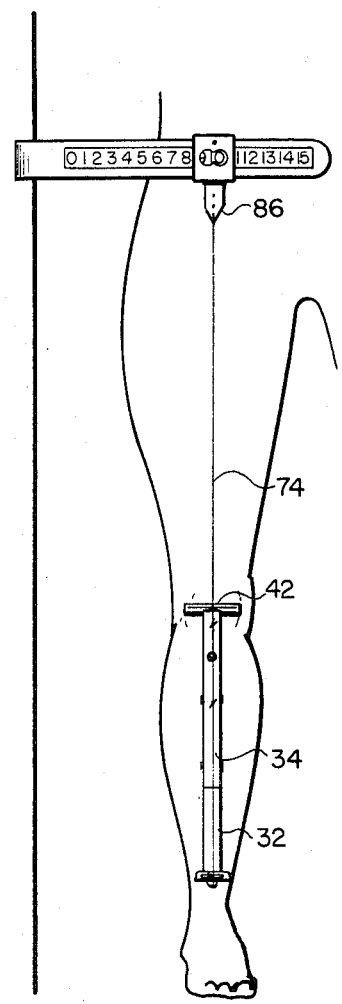
FIG. 5 is a top plan view showing the alignment indicator is use.
Figure 6:
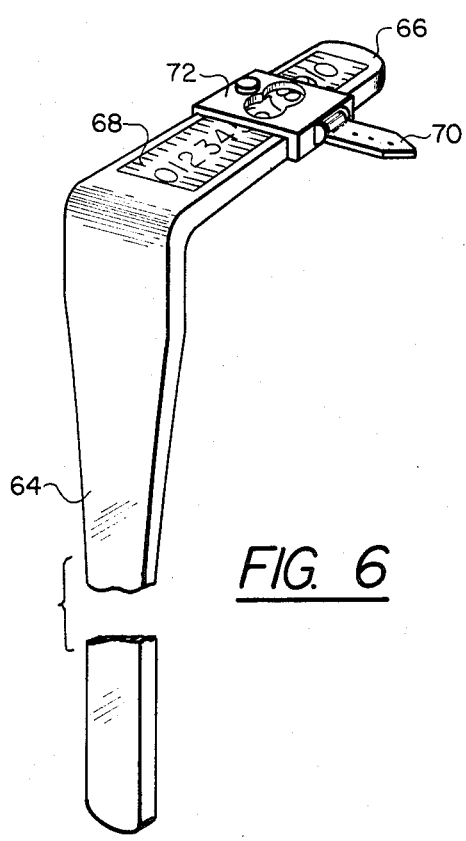
FIG. 6 is a perspective view of the alignment indicator of FIG. 5.

The proper depth and angle of the cut is established prior to insertion of the pins 50 and prior to any cuts being made. The basic cutting guide assembly is first aligned with the load bearing axis of the leg. A system for achieving this alignment is illustrated in FIGS. 5 and 6 and includes a generally L-shaped bracket having a vertical arm 64 for attachment to the side of an operating table with a horizontal arm 66 including a radio opaque indicia or graduated scale 68 and a pointer arm 70 (first alignment member) mounted on a slide 72 for positioning over the hip joint. A flexible line 74 (FIG. 5) is attached at one end to the pointer 70, strung taut through a slot 52a (FIG. 4) in handle 52 and attached at the other end to an arm 75 (second alignment member) on the ankle bracket (FIG. 4). The cutting guide head is then centered over the femoral head and the ankle bracket properly adjusted for proper alignment (with line 74 straight and centered in slot 52a) of the cutting guide. An X-ray can be used to properly locate the hip joint and femoral head with the opaque numbers showing location of the pointer 70.

The length of the member 32, 34 (FIGS. 2 and 3) can be selected by sliding these members upon each other. The distance of the extended member is noted and a mathematical chart is provided which indicates the precise angle of the proximal tibial cut in relation to the indicia of bracket 54. The basic support structure 32, 34 can be adjusted to fit substantially any leg structure and the proper angle thereof adjusted in accordance with the necessary requirements.

Once the base guide and support structure 32, 34 is installed in place, the tibia cut is made and the bone fragments removed. The base guide structure is then removed. The anterior femoral resector/posterior spacer guide, FIGS. 7 and 8, are then applied to the anterior femoral cortex with the knee in flexion. This instrument includes an L-shaped body member 76 having a downwardly extending leg 78 and a spacer and alignment foot 80 for engaging the femur. A cutting guide head 82 having a cutting slot 84 is attached to leg 78 and includes a central knock end pivot 86 and a pair of side anchoring pins 88. The head of the central pivot 86 also serves as a guide for a spacer guide bar 89 which is slideably mounted on the leg 78 and includes a foot 90 extending inward at an 8° angle for engaging the tibia surface 24. The slide bar 89 also includes an upper handle 92 and a slot 94 which engages a guide pin 96 and a clamping pin or stud 98 having a wing nut 100 for securing members 78 and 88 relative to one another.

The spacer guide includes an indicator mark or line 102 or pin 96 which aligns with one of a plurality of marks 104 on slide bar 89 which is calibrated to indicate the size tibia prosthesis will fit in the spacing between the femur and tibia. Upward traction is applied to the distal femur to stretch the ligaments to their optimal length with the knee in flexion. The spacer handle is then depressed until it hits the cut tibial surface. The foot plate must be flat on the tibial surface insuring the knee is in exactly 90° of flexion. The dimensions of the posterior spacer are noted annd the appropriate height of the distal femoral cut is determined. (This correlates to the height of the appropriate tibial plateau). After the anterior condyles have been sectioned to form surface 26 and the reading of the spacer guide taken, the instrument is removed.

A distal femoral condyle cutting guide, as shown in FIGS. 9-11, is then mounted on the upper end of the instrument support frame 34 and the frame reinstalled on the anterior surface of the tibia. The distal femoral condyle guide includes a cutting guide head 106 which is adjustable along frame member 34 to fit the various heights of tibial plateaus. This cutting head 106 is mounted on a generally L-shaped support bar or bracket 108 which slideably mounts on the upper end of the support and guide frame 34 by means of a slot 110 engaging guide pins 112 and clamp stud 114 having a clamp bar 116 and wing nut 118. The lower edges of the support bar 108 serve as indicators for alignment with indicia on body member 34 to indicate the proper setting. With this arrangement, the distal femoral resector or cutting guide can be quickly added or removed from the basic support and guide frame as needed. As will be seen from viewing FIG. 6, the guide slot extends at a preselected angle relative to the guide slot for the tibia. The cutting head 106 includes a guide slot 120 for guiding the cutting of the distal femoral condyle as seen in FIG. 10. The head 106 also includes bores for fixation pins 122 for fixing the instrument in position with the leg straight.

After the resector or cutting guide is in place, the knee is then extended with the weight bearing alignment system in place with the line 74 located over the center of the femoral head. Distal traction is applied to the tibia and to the handle 52 on the tibial resector guide frame and by a firm grasp on the ankle, this will pull the ligaments out to their full anatomical length compatible with correct alignment. Fixation pins 122 are then placed through the holes in the head 106 to maintain alignment while the appropriate cut is then made on the distal femur utilizing the slot in the femoral cutting guide head. The conservative cut, for instance, may correspond to a 22 mm interspacing of the cut surfaces and correspond with a 7.5 mm tibial plateau.

The angle of the guide slots provided for cutting the femoral condyles at a 90 degree angle of the plane of the anterior femoral condyle surface 26. This cut along with the 8 degree posterior slant on the tibial plateau will more correctly correlate the actual anatomical relationship and provide for better flexion of the joint.

Figure 15:
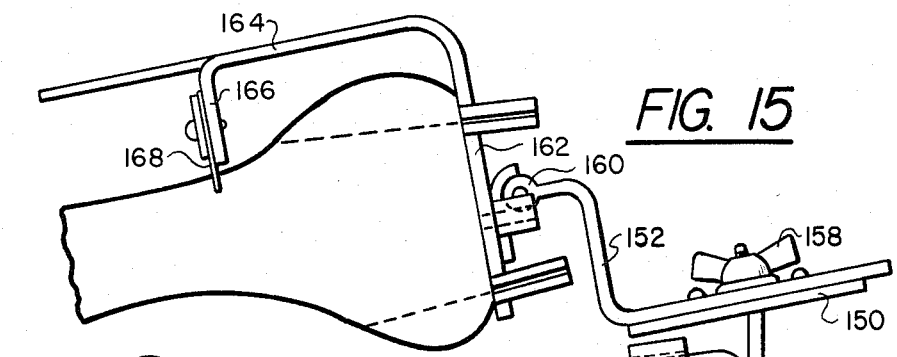
FIG. 15 is a side elevation view of the resection guide of FIG. 14.

The distal femoral cutter guide is then removed and a posterior femoral resector/chamfer guide, as shown in FIGS. 12 and 13, is then placed over the cut surface of the distal femoral condyle. The guide, illustrated in FIGS. 12 and 13, includes a generally rectangular block or body member designated generally by the numeral 124 and being dimensioned in height h to correspond to selected sizes of prosthesis. The guide member 124 has an upper surface 126 that is aligned with the anterior femoral condyle cut or surface 26 and centered on the cut surface 28 of the distal femur. The guide 124 includes fixation pins 128 which are then put in place to fix the guide in place. A pair of cutting guide slots 130 and 132 guide a saw for cutting the posterior condyles at the proper angle and distance h from surface 26 forming surface 30 to thereby receive the proper size prosthesis 18. A chamfer guide slot 134 guides a cutter to chamfer the corner between surface 26 and 28 (FIG. 1). Chamfer guide slots 136 and 138 may be provided for use in cutting the posterior chamfer surface 28 and 30. An alternate embodiment of a combined posterior femoral resector, illustrated in FIGS. 14 and 15, include a generally T-shaped mounting bracket having a vertical leg 144 which detachably mounts by means of a pin 146 and the bolt and wing nut 114 on the upper end of the support and guide frame 34. A generally horizontal plate 150 is secured to the upper end of the vertical leg 144, and on which is detachably mounted a generally L-shaped bracket member 152 which is mounted by means of a pin 154 and stud 156 with a wing nut 158 for releasably mounting the bracket. The generally L-shaped bracket includes a hinge 160 at the inner end which hingedly connects it directly to a body plate 162 which fits up against the cut surface 28 of the distal femoral condyle and includes a forwardly extending alignment arm 164 that extends parallel to the femur and includes a fixed bracket member 166 extending downward with a pivotal arcuate shaped spacer member 168 that is pivotally mounted on the lower end of the downwardly extending arm and engaging the femur for accommodating alignment of the guide member and aligning it parallel to the femur. Once the anterior-posterior femur resector guide is in place, pins 170 and 172 are inserted through bores in the face plate and into the end of the femur for fixing the cutter guide in place. The adjustment nuts 114 and 158 are then tightened. The appropriate cuts are made to remove the necessary portion of the posterior femoral condyles and the appropriate chamfers for the specific sized prosthesis is made. The resector includes guide slots formed between pairs of bars or plates and are appropriately spaced and angled to provide the required angle of cut with respect to the previously cut distal femoral section. These slots are formed between upper bars 174 and 176 and lower spaced bars 178 and 180. Once these cuts are made, all the cutting guide jigs are removed.

Placement of the prosthesis is then begun by first inserting a trial prosthesis onto the femur and tapping it gently into place. The holes for the femoral prosthesis pegs are tamped by a punch through the holes in the trial prosthesis.

Figure 17:
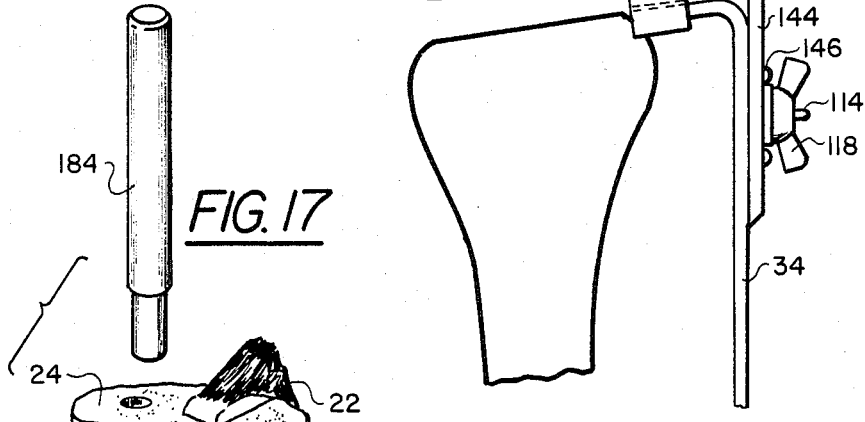
FIG. 17 is a perspective view of a tibial anterior spike broach in accordance with the invention.
Figure 16:
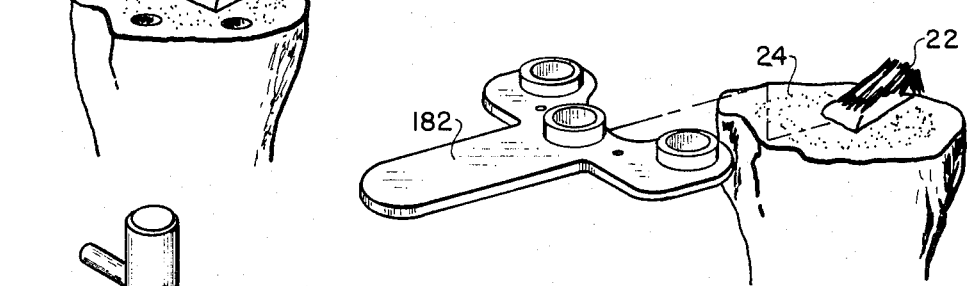
FIG. 16 is a perspective view of a tibial drill guide.
Figure 18:
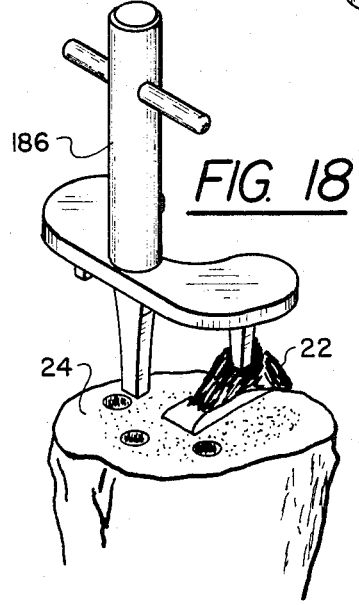
FIG. 18 is a perspective view of a tibial finish broach.

Preparation of the tibial plateau is then carried out by placing a selected tibial drill guide or template 182 (FIG. 16) having the appropriate guide bores as illustrated over the tibial plateau and drilling or tamping by a punch through these holes in the template to create initial holes. A longer specifically designed tamp 184 (FIG. 17) is then placed in the anterior hole and tapped gently into place. This provides an initial reaming of the anterior tibial hole to accept a final finish broach 186 (FIG. 18). The tibial plateau finish broach is then forced into place accurately forming the holes to the desired final size and configuration and compacting the bone in the proximal tibia. The holes in the tibia are sized to accept sufficient bonding cement and to allow minor adjustment of the tibial prosthesis. The trial tibial prosthesis is then placed in position and the trial prosthesis components then tested. Prior to cementing in place an X-ray can be taken to confirm proper alignment and fit.

The tibial component of the prosthesis is first placed into the bone and bonded into place with a suitable cement, preferably, methyl-methacrylate. Any excess cement is removed and the tibial component held firmly to the cut tibia, with the knee in flexion, until the cement hardens. The knee is carefully subluxed and excess cement removed from about the posterior recess of the tibial condyles. Special posterior collateral ligament hand retractors (not shown) are used in this process.

Figure 19:
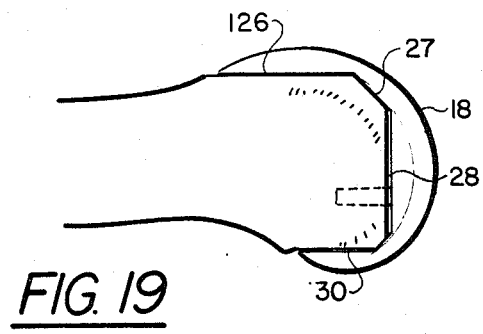
FIG. 19 is a side elevation view of the femoral prosthesis shown in place.

The femoral component is now fitted and cemented in position on the distal femur as seen in FIG. 19. The preferred prosthesis 18 as shown in FIG. 19 has the corners chamfered between the flat surfaces that are to fit surfaces 26, 28, and 30 of the distal femur. Excess cement is removed after the femoral component is properly positioned. The knee is then gently flexed and extended and pressure is applied to the patellar prosthesis to correctly center the patellar prosthesis. This also centers the tibia on the femur. Proper adjustments with flexion-extension with the components in place are utilized for obtaining ideal alignment of the knee. The knee is then acutely fixed and the cement removed from the posterior femoral condyles by special cement removing instruments (not shown) that are curved to readily gain access to the recesses that are not readily visible.

In summary, the instrument system as described and used herein, provides an alignment system that accurately aligns the transverse axis of the knee with the true weight bearing axis of the anatomy. It allows the surgeon to make accurate corrections for anatomical variations if present. It also provides a system that in trial has been found to be extremely accurate and provides an accurate and uniform fit of the prosthesis.

While I have illustrated and described my invention by specific embodiments it is to be understood that numerous changes and modifications may be made therein without departing from the spirit and scope of the invention as defined in the appended claims.

I claim:

1. A system of instruments for assisting in performing knee replacement surgery, comprising;
    a cutting guide for guiding an instrument for cutting a knee joint surface; and means for precisely aligning said cutting guide with respect to the true weight bearing axis of the leg in which the knee is to be replaced, comprising an extensible member having said cutting guide attached at one end thereof; and an adjustable ankle means at the other end of said body member having means engaging the ankle.

2. The system of claim 1 wherein said cutting guide is a tibial cutting guide adapted to guide an instrument for cutting the tibial plateau.

3. The system of claim 1 wherein said cutting guide is a distal femoral cutting guide for guiding an instrument for cutting the distal end of a femur.

4. The system of claim 1 and further including a combined anterior femoral condyle resector guide and posterior condyle spacer guide means for guiding the accurate removal of an anterior portion of the femoral condyles and for establishing the size of the optimal tibial prosthesis.

5. The system of claim 4 wherein said combined resector guide and spacer guide means includes:
    a generally L-shaped body member having a leg portion for alignment with a femur and a foot for extending across the distal femur, and
    cutting guide slot means mounted on said foot for guiding a surgical instrument for cutting the anterior portion of the femoral condyles.

6. The system of claim 5 wherein said spacer guide means includes a slide member slideably mounted on said foot member and including a foot plate for engaging the tibia surface, and
    indicia means located on said foot member or said slide member for indicating the optimal size prosthesis for fitting the space between the femur and tibia in 90° of flexion.

7. The system of claim 1 further including adjusting means for adjusting the angle of said cutting guide with respect to the weight bearing axis of the leg.

8. The system of claim 7 wherein
    said extensible body member comprises: an upper elongated body member; a lower body member; and means for adjustably securing said upper and lower body members; and
    said adjusting means comprises means for laterally adjusting said ankle means with respect to said lower body member and including indicia means related to extensible positions of said body member for defining angles of adjustment.

9. The system of claim 3 or 8 including a posterior femoral resector and chamfer guide, said guide having a generally rectangular configuration with a flat surface for engagement with a flat surface of a previously sectioned end of a distal femur, an upper aligning surface for alignment with a previously sectioned anterior position of a femur, and
    cutting guide slot means for guiding the cutting of a posterior portion of the femoral condyles at a selected angle and distance relative to the surface of said previously sectioned femur.

10. The system of claim 9 wherein said resector and chamfer guide includes a chamfer guide slot for establishing a chamfer between an anterior portion of the femoral condyle surface and the distal femoral surface.

11. The system of claim 7 wherein said means for adjusting includes a slide member adjustably secured to said extensible body member.

12. The system of claim 7 including a combined anterior and posterior femoral condyle resection guide,
    said combined guide including a femoral alignment guide member having a femoral engaging support member and a cutting guide head having a first cutting guide member for selectively guiding a cutting instrument for guiding the cutting of an anterior portion of the femoral condyles.

13. The system of claim 12 wherein said combined anterior and posterior femoral condyle resection guide, is detachably mounted on said extensible body member.

14. The system of claim 1 wherein said means for aligning includes means for aligning with the hip and the ankle associated with the leg in which the knee is to be replaced.

15. The system of claim 1 wherein said means for aligning includes:
    an extensible body member adapted to be placed along the leg in which the knee is to be replaced having a handle extending substantially in a direction opposite from the direction of said leg;
    a means for connecting two points along said weight bearing axis of the leg; and
    a means in said handle for cooperating with said means for connecting to align said cutting guide.

16. The system of claim 1 wherein said means for aligning includes:
    a first alignment member;
    a second alignment member; and
    a means for precisely locating said alignment members relative to the true weight bearing axis of the leg in which the knee is to be replaced.

17. A system of instruments in accordance with claim 16 wherein said means for locating comprises:
    means for locating said first alignment member in relation to the hip joint; and
    means for locating said second alignment member in relation to the ankle joint; and
    said means for aligning further includes a means for positioning said cutting guide in relation to said first and second alignment members.

18. A system of instruments according to claim 16 wherein said first alignment member includes a radiopaque indicator means.

19. A system of instruments according to claim 18 wherein said means for locating said first member includes a scale having radiodetectable indicia.

20. A system of instruments according to claim 19 wherein said means for locating said first member further comprises a means for attaching said scale to an operating table and a slide means for moving along said scale, and said indicator means is attached to said slide means.

21. A system of instruments according to claim 16 wherein said means for locating said second alignment member comprises a means for engaging the ankle area of the leg.

22. A system of instruments according to claim 21 wherein said means for aligning further includes:
a means for adjusting the position of said means for engaging with respect to said cutting guide, and
an indicator having indicia marks for indicating the relative position of said means for engaging with respect to said cutting guide.

23. A system of instruments according to claim 16 wherein said means for aligning further comprises:
a means for defining a straight line between said first and second member; and
a means for locating said cutting guide along said straight line.

24. A system in accordance with claim 23 wherein said means for defining a straight line comprises an extensible means for extending between said first and second members.

25. A system in accordance with claim 24 wherein said means for locating said cutting guide along said straight line comprises a slotted means for accepting said extensible means, said slotted means being connected to said cutting guide.

26. A system in accordance with claim 23 wherein said means for aligning further comprises a means for adjusting for valgus and varus alignment of said knee.

27. A system of instruments according to claim 26 wherein said means for locating a second alignment member comprises a means for engaging the ankle area of the leg, and said means for adjusting comprises a means for adjustably securing said second member in relation to said cutting guide.

28. A system of instruments in accordance with claim 27 wherein said means for aligning said cutting guide further includes means for determining the amount of adjustment of said second member appropriate for different leg lengths.

29. A system of instruments according to claim 16 wherein said cutting guide comprises a means for guiding an instrument for cutting the distal end of the femur.

30. A system in accordance with claim 16 and further including an anterior femoral condyle resector guide means for guiding the accurate removal of an anterior portion of the femoral condyles.

31. A system in accordance with claim 30 wherein said anterior femoral condyle resector guide comprises a generally L-shaped body member having a leg poortion for alignment with the femur and a foot for extending across the distal femur, and having a cutting guide slot in said foot for guiding a surgical instrument for cutting an anterior portion of the femoral condyles.

32. A system in accordance with claim 1 wherein said means for aligning includes means for adjusting to fit substantially any leg structure.

33. a system in accordance with claim 1 wherein said means for aligning comprises a means for adjusting for valgus and varus alignment of said knee.

34. A system in accordance with claim 1 and further including a spacer guide means for establishing the size of the optimal prosthesis for fitting the space between the femur and the tibia.

35. A system in accordance with claim 34 wherein said spacer guide comprises a generally L-shaped body member having a leg portion for alignment with the femur and a foot for extending across the distal end of the femur.

36. A system in accordance with claim 35 wherein said spacer guide includes:
a slide member slideably mounted on said foot member and having a foot plate for engaging a surface of the tibia of the leg in which the knee is to be replaced; and
indicia means located on either said foot member or said slide member for indicating the optimal size prosthesis for fitting the space between the femur and tibia.

37. A method of cutting the bones associated with the knee joint in replacement surgery including the steps of:
providing an instrument comprising a body member having a slotted ankle bracket attached to one end and a cutting guide attached to the other end;
engaging the ankle of the leg on which the knee is to be replaced in the slot of the slotted ankle bracket, aligning the cutting guide with respect to the weight bearing axis of the leg, and cutting a surface of the knee joint while guiding the cutting instrument with said guide.

38. The method of claim 37 wherein the step of aligning said cutting guide includes the steps of moving one end of the body member of said cutting guide in a direction substantially transverse to the long axis of the tibia; and
securing said body portion to said ankle bracket.

39. The method of claim 38 wherein the step of providing includes providing a hip guide member and an extensible member, and the step of aligning said cutting guide includes the steps of:
locating the hip guide member in relation to the hip joint, and
extending the extensible member from said hip joint guide member to said ankle bracket.

40. A system of instruments for assisting in performing knee replacement surgery, said system including:
a cutting guide for guiding an instrument for cutting a surface of the knee joint;
indicia means for aligning the cutting guide with the load bearing axis of the leg;
a first alignment member and means for locating said first alignment member in relation to said indicia means;
a second alignment member and means for locating said second alignment member in relation to said ankle; and
elongated means connected between said first alignment member and said second alignment member for correctly locating said cutting guide along a straight line defined by said elongated means.

41. A system of instruments for assisting in the performing of knee replacement surgery, said system including;
   a cutting guide for guiding an instrument for cutting a surface of a knee joint; and
   extensible means for aligning the cutting guide with the load bearing axis of the leg, said extensible means connecting a point above the knee joint to a point below the knee joint and being sufficiently extensible to permit the movement of the points with respect to each other by the surgeon while continuing to connect said points; said extensible means including flexible means interconnecting said two points, said extensible means including a handle with a slot, said flexible means extending through said slot.

42. A method of cutting bones associated with the knee joint in knee replacement surgery including the steps of:
   providing a cutting means and a cutting guide including an ankle bracket;
   locating the true weight bearing axis of the leg in which the knee is to be replaced by engaging the ankle of the leg with the bracket;
   aligning the cutting guide with respect to the located axis; and
   cutting a surface of the knee joint while guiding the cutting means with the aligned cutting guide.

43. A method in accordance with claim 42 wherein said step of providing includes providing a hip indicator member and said step of locating comprises:
   placing the hip indicator member in the vicinity of the hip; and
   using leg penetrating radiation to determine the position of said indicator in relation to the hip.

44. A method in accordance with claim 42 wherein said step of cutting comprises cutting the distal end of the femur.

45. A method in accordance with claim 42 wherein the step of providing includes providing a hip locator member and the step of locating includes the step of attaching the hip locator member to the operating table.

46. A method in accordance with claim 42 wherein said step of providing includes providing an extensible connector and said step of aligning includes the steps of:
   connecting the extensible connector between a point above the knee and a point below the knee; and
   extending the knee ligaments while using said extensible connector to align the cutting guide.

47. A method in accordance with claim 42, further including the step of adjusting said ankle bracket to correct the valgus or varus position of the knee.

48. The method of claim 42, wherein said locating step includes the step of connecting a locating means between two points on said cutting guide, and said aligning step includes the step of aligning said cutting guide in a pre-determined relationship with said locating means.

49. A method of cutting bones associated with the knee joint in knee replacement surgery including the steps of:
   providing a cutting means and a cutting guide including hip locator member;
   locating the true weight bearing axis of the leg in which the knee is to be replaced by attaching the hip locator member to the operating table;
   aligning the cutting guide with respect to the located axis; and
   cutting a surface of the knee joint while guiding the cutting means with the aligned cutting guide.

50. The method of claim 49, wherein said locating step includes the step of connecting a locating means between two points on said cutting guide, and said aligning step includes the step of aligning said cutting guide in a pre-determined relationship with said locating means.

* * * * *